United States Patent
Cordonnier

(10) Patent No.: US 12,427,025 B2
(45) Date of Patent: *Sep. 30, 2025

(54) SYSTEMS AND METHODS FOR MULTI-PLANAR ORTHOPEDIC ALIGNMENT

(71) Applicant: Carlsmed, Inc., Carlsbad, CA (US)

(72) Inventor: Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 1110 days.

This patent is subject to a terminal disclaimer.

(21) Appl. No.: 17/369,777

(22) Filed: Jul. 7, 2021

(65) Prior Publication Data
US 2022/0000625 A1    Jan. 6, 2022

Related U.S. Application Data

(63) Continuation of application No. 16/207,116, filed on Dec. 1, 2018, now Pat. No. 11,083,586.
(Continued)

(51) Int. Cl.
*A61F 2/30*    (2006.01)
*A61F 2/44*    (2006.01)

(52) U.S. Cl.
CPC ........ *A61F 2/30942* (2013.01); *A61F 2/4455* (2013.01); *A61F 2002/30593* (2013.01);
(Continued)

(58) Field of Classification Search
CPC .... A61F 2/30942; A61F 2/4455; A61B 34/20; A61B 34/25; A61B 34/30
See application file for complete search history.

(56) References Cited

U.S. PATENT DOCUMENTS

| 4,704,686 A | 11/1987 | Aldinger |
| 4,936,862 A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Si Ming Ku
(74) *Attorney, Agent, or Firm* — Perkins Coie LLP

(57) ABSTRACT

A method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

24 Claims, 9 Drawing Sheets

Related U.S. Application Data

(60) Provisional application No. 62/594,510, filed on Dec. 4, 2017.

(52) U.S. Cl.
CPC .............. *A61F 2002/30943* (2013.01); *A61F 2002/30948* (2013.01); *A61F 2002/30952* (2013.01); *A61F 2002/30953* (2013.01); *A61F 2002/30985* (2013.01); *A61F 2/446* (2013.01); *A61F 2/4465* (2013.01); *A61F 2/447* (2013.01)

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,214,016 B2 | 7/2012 | Lavallee |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,343,221 B2 | 1/2013 | Trieu |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,592,095 B2 | 3/2017 | Panescu |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,022,192 B1 | 7/2018 | Ummalaneni |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| 11,278,413 B1 | 3/2022 | Lang |

(56) References Cited

U.S. PATENT DOCUMENTS

| | | |
|---|---|---|
| D958,151 S | 7/2022 | Casey et al. |
| 11,806,241 B1 | 11/2023 | Hussain |
| 11,857,264 B2 | 1/2024 | Roh et al. |
| 2002/0007294 A1 | 1/2002 | Bradbury et al. |
| 2004/0104512 A1 | 6/2004 | Eidenschink |
| 2004/0171924 A1 | 9/2004 | Mire et al. |
| 2005/0049590 A1 | 3/2005 | Alleyne et al. |
| 2005/0234555 A1 | 10/2005 | Sutton et al. |
| 2005/0271996 A1 | 12/2005 | Sporbert et al. |
| 2005/0273170 A1 | 12/2005 | Navarro et al. |
| 2005/0277934 A1 | 12/2005 | Vardiman |
| 2006/0009780 A1 | 1/2006 | Foley |
| 2007/0118243 A1 | 5/2007 | Schroeder |
| 2007/0272747 A1 | 11/2007 | Woods et al. |
| 2007/0276369 A1 | 11/2007 | Allard et al. |
| 2007/0276501 A1 | 11/2007 | Betz |
| 2008/0161680 A1 | 7/2008 | von Jako |
| 2008/0195240 A1 | 8/2008 | Martin |
| 2008/0227047 A1 | 9/2008 | Lowe |
| 2008/0294265 A1 | 11/2008 | Warkentine et al. |
| 2009/0062739 A1 | 3/2009 | Anderson |
| 2010/0100011 A1 | 4/2010 | Roche |
| 2010/0191088 A1 | 7/2010 | Anderson |
| 2010/0217270 A1 | 8/2010 | Polinski |
| 2010/0217336 A1 | 8/2010 | Crawford et al. |
| 2010/0292963 A1 | 11/2010 | Schroeder |
| 2010/0324692 A1 | 12/2010 | Uthgenannt |
| 2011/0196451 A1 | 8/2011 | Hill |
| 2011/0218545 A1 | 9/2011 | Catanzarite et al. |
| 2011/0269104 A1 | 11/2011 | Berckmans |
| 2011/0301710 A1 | 12/2011 | Mather et al. |
| 2012/0010710 A1 | 1/2012 | Frigg |
| 2012/0084064 A1 | 4/2012 | Dzenis et al. |
| 2012/0116203 A1 | 5/2012 | Vancraen |
| 2012/0150243 A9 | 6/2012 | Crawford |
| 2012/0179258 A1 | 7/2012 | Glazer et al. |
| 2012/0191192 A1 | 7/2012 | Park |
| 2012/0287238 A1 | 11/2012 | Onishi |
| 2012/0296433 A1 | 11/2012 | Farin |
| 2012/0310364 A1 | 12/2012 | Li et al. |
| 2012/0322018 A1 | 12/2012 | Lowe |
| 2013/0079680 A1 | 3/2013 | Stein |
| 2013/0211531 A1 | 8/2013 | Steines et al. |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0135940 A1 | 5/2014 | Goldstein |
| 2014/0164022 A1 | 6/2014 | Reed |
| 2014/0244220 A1 | 8/2014 | McKinnon |
| 2014/0263674 A1 | 9/2014 | Cerveny |
| 2014/0272881 A1 | 9/2014 | Barsoum |
| 2014/0277487 A1 | 9/2014 | Davenport et al. |
| 2014/0350614 A1 | 11/2014 | Frey |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0012753 A1 | 1/2016 | Mehdian |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0081810 A1 | 3/2016 | Reiley et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0191887 A1 | 6/2016 | Casas |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354213 A1 | 12/2016 | Cowan |
| 2016/0361025 A1 | 12/2016 | Reicher |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0046486 A1 | 2/2017 | Cunningham |
| 2017/0061375 A1 | 3/2017 | Laster |
| 2017/0068792 A1 | 3/2017 | Reiner |
| 2017/0112548 A1 | 4/2017 | Alamin et al. |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0196499 A1 | 7/2017 | Hunter |
| 2017/0216047 A1 | 8/2017 | Hawkes et al. |
| 2017/0220740 A1 | 8/2017 | D'Urso |
| 2017/0242107 A1 | 8/2017 | Dussan et al. |
| 2017/0252107 A1 | 9/2017 | Turner et al. |
| 2017/0258526 A1 | 9/2017 | Lang |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0360358 A1 | 12/2017 | Amiot |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0247020 A1 | 8/2018 | Itu et al. |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0325599 A1 | 11/2018 | Seo |
| 2018/0338841 A1 | 11/2018 | Miller et al. |
| 2018/0360609 A1 | 12/2018 | Steines et al. |
| 2019/0039286 A1 | 2/2019 | Tempco et al. |
| 2019/0065685 A1 | 2/2019 | Pickover |
| 2019/0069956 A1 | 3/2019 | Ryan et al. |
| 2019/0088371 A1 | 3/2019 | Casey et al. |
| 2019/0099221 A1 | 4/2019 | Schmidt et al. |
| 2019/0201106 A1 | 7/2019 | Siemionow |
| 2019/0209731 A1 | 7/2019 | Keyak et al. |
| 2019/0262084 A1 | 8/2019 | Roh et al. |
| 2019/0266597 A1 | 8/2019 | Mohtar |
| 2019/0282367 A1 | 9/2019 | Casey et al. |
| 2019/0321132 A1 | 10/2019 | Weir |
| 2019/0321193 A1 | 10/2019 | Casey et al. |
| 2019/0328929 A1 | 10/2019 | Kugler et al. |
| 2019/0333622 A1 | 10/2019 | Levin |
| 2019/0350720 A1 | 11/2019 | Koffler et al. |
| 2019/0354693 A1 | 11/2019 | Yoon |
| 2019/0380782 A1 | 12/2019 | McAfee et al. |
| 2019/0380792 A1 | 12/2019 | Poltaretskyi et al. |
| 2019/0388131 A1 | 12/2019 | Mehl et al. |
| 2020/0021570 A1 | 1/2020 | Lin |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0188130 A1 | 6/2020 | Jebsen et al. |
| 2020/0258605 A1 | 8/2020 | Blechman |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0169576 A1 | 6/2021 | Ryan et al. |
| 2021/0192759 A1 | 6/2021 | Lang |
| 2021/0210189 A1 | 7/2021 | Casey et al. |

(56) References Cited

U.S. PATENT DOCUMENTS

| | | |
|---|---|---|
| 2021/0257094 A1 | 8/2021 | Takemoto et al. |
| 2021/0287770 A1 | 9/2021 | Anderson |
| 2021/0290319 A1 | 9/2021 | Poltaretskyi et al. |
| 2021/0315706 A1 | 10/2021 | Noshchenko et al. |
| 2021/0378752 A1 | 12/2021 | Paul |
| 2021/0382457 A1 | 12/2021 | Roh et al. |
| 2022/0000556 A1 | 1/2022 | Casey et al. |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0313362 A1 | 10/2022 | Casey et al. |
| 2023/0023440 A1 | 1/2023 | Casey et al. |
| 2023/0087107 A1 | 3/2023 | Casey et al. |
| 2023/0138162 A1 | 5/2023 | Winston |
| 2023/0255690 A1 | 8/2023 | Castro |
| 2024/0016547 A1 | 1/2024 | Casey et al. |
| 2024/0016614 A1 | 1/2024 | Casey et al. |
| 2024/0065767 A1 | 2/2024 | Cordonnier |
| 2024/0079114 A1 | 3/2024 | Casey et al. |
| 2024/0138919 A1 | 5/2024 | Casey et al. |
| 2024/0138921 A1 | 5/2024 | Roh et al. |
| 2024/0225531 A1 | 7/2024 | Casey et al. |
| 2024/0261029 A1 | 8/2024 | Casey et al. |
| 2024/0319709 A1 | 9/2024 | Roh et al. |
| 2024/0341960 A1 | 10/2024 | Casey |
| 2024/0374316 A1 | 11/2024 | Casey et al. |
| 2024/0374389 A1 | 11/2024 | Casey et al. |
| 2025/0025309 A1 | 1/2025 | Casey et al. |
| 2025/0114145 A1 | 4/2025 | Casey et al. |

FOREIGN PATENT DOCUMENTS

| | | |
|---|---|---|
| CN | 204468348 U | 7/2015 |
| CN | 105796214 A | 7/2016 |
| CN | 106202861 | 12/2016 |
| CN | 107220933 | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 | 11/2021 |
| EP | 3120796 A1 | 1/2017 |
| JP | 2011517996 A | 6/2011 |
| JP | 2012531265 A | 12/2012 |
| JP | 2013523415 A | 6/2013 |
| JP | 2016503319 A | 2/2016 |
| JP | 2016536051 A | 11/2016 |
| JP | 2016540610 A | 12/2016 |
| JP | 2017510307 A | 4/2017 |
| WO | 9507509 | 3/1995 |
| WO | 2004110309 A2 | 12/2004 |
| WO | 2008027549 A2 | 3/2008 |
| WO | 2010151564 A1 | 12/2010 |
| WO | 2011080260 A1 | 7/2011 |
| WO | 2012154534 | 11/2012 |
| WO | 2014145267 A1 | 9/2014 |
| WO | 2014180972 A2 | 11/2014 |
| WO | 2015075423 A2 | 5/2015 |
| WO | 2016102025 A1 | 6/2016 |
| WO | 2016172694 A1 | 10/2016 |
| WO | 2017116346 A1 | 7/2017 |
| WO | 2018193316 A2 | 10/2018 |
| WO | 2019112917 A1 | 6/2019 |
| WO | 2019148154 A1 | 8/2019 |
| WO | 2019165152 A1 | 8/2019 |
| WO | 2019241167 A1 | 12/2019 |
| WO | 2020055874 A1 | 3/2020 |
| WO | 2022045956 | 3/2022 |
| WO | 2023034405 A1 | 3/2023 |

OTHER PUBLICATIONS

Extended European Search Report for European Application No. 18885367.5, mailed Aug. 16, 2021, 8 pages.
International Search Report and Written Opinion for International Application No. PCT/US19/50885, mailed Jan. 28, 2020, 21 pages.
International Search Report and Written Opinion for International Application No. PCT/US19/63855, mailed Feb. 14, 2020, 15 pages.
International Search Report and Written Opinion for International Application No. PCT/US21/44878, mailed Nov. 16, 2021, 18 pages.
International Search Report and Written Opinion for International Application No. PCT/US21/45503, mailed Jan. 11, 2022, 19 pages.
International Search Report and Written Opinion for International Patent Application No. PCT/US2018/063530, mailed Feb. 12, 2019, 16 pages.
International Search Report and Written Opinion for International Patent Application No. PCT/US21/12065, mailed Apr. 29, 2021, 19 pages.
International Search Report and Written Opinion for International Patent Application No. PCT/US21/59837, mailed Feb. 7, 2022, 19 pages.
Majdouline et al., "Preoperative assessment and evaluation of instrumentation strategies for the treatment of adolescent idiopathic scoliosis: computer simulation and optimization." Scoliosis 7, 21 (2012), pp. 1-8.
Materialise Mimics, "Efficiently turn scans into accurate virtual 3D models," Retrieved on Nov. 1, 2019 at www.materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.
U.S. Appl. No. 15/958,409 for Ryan filed Apr. 21, 2017.
Clement, R.C. et al., "A proposed set of metrics for standardized outcome reporting in the management of low back pain." Acta Orthopaedica. Sep. 3, 2015;86 (5); 523-33.
Examination Report for European Application No. 19859930.0, mailed Mar. 12, 2024, 5 pages.
Godil, S.S. et al., "Determining the quality and effectiveness of surgical spine care: patient satisfaction is not a valid proxy." The Spine Journal: Off. Jour. Of the North American Spine Society. May 16, 2013; 13(9): 1006-12.
Hartzler, A. et al., "Integrating Patient-Reported Outcomes into Spine Surgical Care through Visual Dashboards: Lessons Learned from Human-Centered Design." eGEMs. 2015;3(2), 20 pages.
Office Action for Japanese Application No. 2021-539471, mailed May 30, 2024, 4 pages, English Translation.
Office Action for Japanese Application No. 2022-541805, mailed Jul. 25, 2024, 6 pages, English Translation.
de Beer, N. et al., "Patient-specific intervertebral disc implants using rapid manufacturing technology." Rapid Prototyping Journal 19.2: 2013, 126-139.
Haglin, J.M. et al., "Patient-specific orthopaedic implants." Orthopaedic surgery 8.4: 2016, 417-424.
Eshkalak, S.K. et al., "The role of three-dimensional printing in healthcare and medicine." Materials and Design 194, Jul. 10, 20202, 15 pages.
Extended European Search Report for European Application No. 19859930.0, mailed Jun. 22, 2022, 7 pages.
International Search Report and Written Opinion for International Patent Application No. PCT/US21/60074, mailed Mar. 17, 2022, 21 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 17/463,054 for Casey et al., filed Aug. 31, 2021.
U.S. Appl. No. 17/518,524 for Cordonnier, filed Nov. 3, 2021.
U.S. Appl. No. 17/678,874 for Cordonnier, filed Feb. 23, 2022.
U.S. Appl. No. 17/702,591 for Roh et al., filed Mar. 23, 2022.
U.S. Appl. No. 17/835,777 for Cordonnier, filed Jun. 8, 2022.
U.S. Appl. No. 17/838,727 for Casey et al., filed Jun. 13, 2022.
U.S. Appl. No. 17/842,242 for Cordonnier, filed Jun. 16, 2022.
U.S. Appl. No. 17/851,487 for Cordonnier, filed, Jun. 28, 2022.
U.S. Appl. No. 17/856,625 for Cordonnier, filed, Jul. 1, 2022.

(56) References Cited

OTHER PUBLICATIONS

U.S. Appl. No. 17/867,621 for Cordonnier, filed, Jul. 18, 2022.
U.S. Appl. No. 17/875,699 for Casey et al., filed, Jul. 28, 2022.
U.S. Appl. No. 17/878,633 for Cordonnier, filed, Aug. 1, 2022.
U.S. Appl. No. 17/880,277 for Casey et al., filed, Aug. 3, 2022.
Examination Report for European Application No. 19890663.8, mailed Feb. 7, 2024, 4 pages.
Extended European Search Report for European Application No. 19890663.8, mailed Jul. 29, 2022, 8 pages.
Extended European Search Report for European Application No. 21738283.7, mailed Jan. 2, 2024, 9 pages.
Hammoudeh J.A. et al., "Current Status of Surgical Planning for Orthognathic Surgery: Traditional Methods versus 3D Surgical Planning." PRS Global Open, Feb. 2015, 11 pages.
Harrysson, O. et al., "Custom-designed orthopedic implants evaluated using finite element analysis of patient-specific computed tomography data: femoral-component case study." BMC Musculoskeletal Disorders. Dec. 2007, 8:91, 10 pages.
International Search Report and Written Opinion for International Application No. PCT/US22/37640, mailed Nov. 15, 2022, 13 pages.
International Search Report and Written Opinion for International Patent Application No. PCT/US23/36137, mailed Mar. 5, 2024, 20 pages.
Mangano C. et al., "Combining Intraoral Scans, Cone Beam Computed Tomography and Face Scans: The Virtual Patient." Journal of Craniofacial Surgery, Nov. 1, 2018:29(8): 27 pages.
Office Action for Japanese Application No. 2020-550591, mailed Dec. 26, 2022, 4 pages, English Translation.
Office Action for Japanese Application No. 2020-550591, mailed Sep. 21, 2023, 4 pages, English Translation.
Office Action for Japanese Application No. 2021-539471, mailed Aug. 3, 2023, 5 pages, English Translation.
Office Action for Japanese Application No. 2021-531331, mailed Oct. 23, 2023, 2 pages, English Translation.
Swennen, G.R.J. et al., "Three-Dimensional Treatment Planning of Orthognathic Surgery in the Era of Virtual Imaging." American Assoc. of Oral and Maxillofacial Surgeons 67:2080-2092, 2009.
U.S. Appl. No. 18/071,566 for Casey et al., filed Nov. 29, 2022.
Examination Report mailed Apr. 8, 2025 for Australian Patent Application No. 2021205797, 3 pages.
Examination Report mailed Apr. 22, 2025 for Australian Patent Application No. 2021205797, 3 pages.
Farhadi, F. et al., "Applications of artificial intelligence in orthopaedic surgery." Frontiers in Medical Technology, Dec. 15, 2022, 14 pages.
Georgiakakis, E.C.T., et al., "Artificial intelligence in planned orthopaedic care." SICOT-J, 10, 2024, 8 pages.
Office Action for Japanese Application No. 2022-541805, mailed Apr. 21, 2025, 6 pages, English Translation.

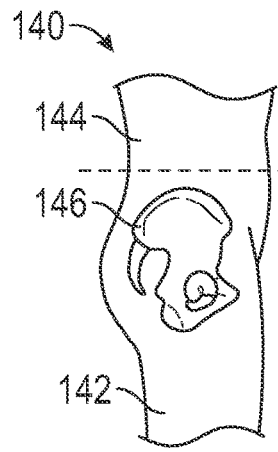
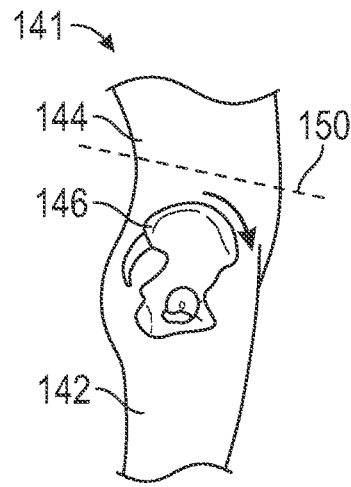
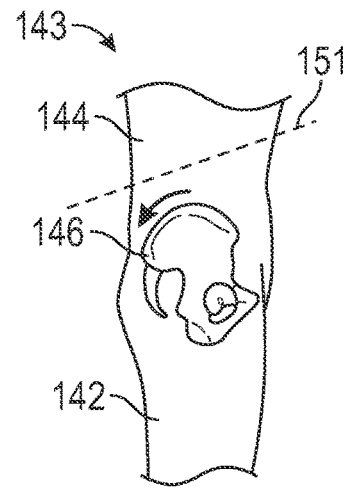
FIG. 25  FIG. 26  FIG. 27
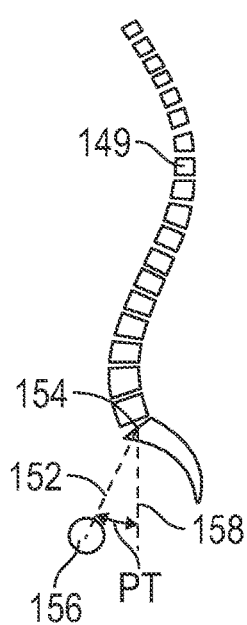
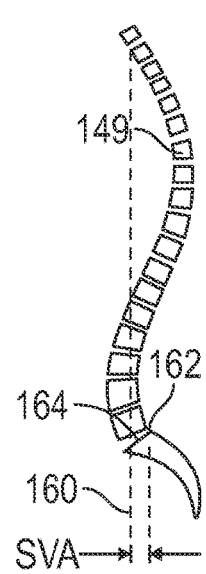
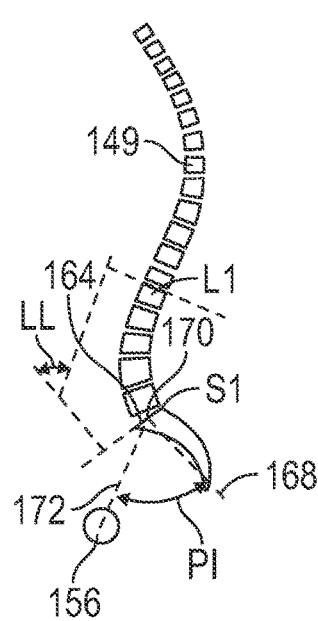
FIG. 28  FIG. 29  FIG. 30

SYSTEMS AND METHODS FOR MULTI-PLANAR ORTHOPEDIC ALIGNMENT

CROSS-REFERENCE TO RELATED APPLICATION(S)

This application is a continuation of U.S. patent application Ser. No. 16/207,116, filed on Dec. 1, 2018 (now U.S. Pat. No. 11,083,586), which claims the benefit of priority to U.S. Provisional Patent Application No. 62/594,510, filed on Dec. 4, 2017, both of which are incorporated herein by reference in their entireties for all purposes.

TECHNICAL FIELD

The field of the invention generally relates to patient-specific implants, including patient-specific orthopedic implants, and methods for designing and producing them.

BACKGROUND

Orthopedic implants are used to correct a variety of different maladies. Orthopedic surgery utilizing orthopedic implants may include one of a number of specialties, including: hand surgery, shoulder and elbow surgery, total joint reconstruction (arthroplasty), skull reconstruction, pediatric orthopedics, foot and ankle surgery, spine surgery, musculoskeletal oncology, surgical sports medicine, and orthopedic trauma. Spine surgery may encompass one or more of the cervical, thoracic, lumbar spine, or the sacrum, and may treat a deformity or degeneration of the spine, or related back pain, leg pain, or other body pain. Irregular spinal curvature may include scoliosis, lordosis, or kyphosis (hyper or hypo), and irregular spinal displacement may include spondylolisthesis. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion).

One goal of interbody fusion is to grow bone between vertebra in order to seize (e.g., lock) the spatial relationships in a position that provides enough room for neural elements, including exiting nerve roots. An interbody implant device (interbody device, interbody implant, interbody cage, fusion cage, or spine cage) is a prosthesis used in spinal fusion procedures to maintain relative position of vertebra and establish appropriate foraminal height and decompression of exiting nerves. Each patient may have individual or unique disease characteristics, but most implant solutions include implants (e.g., interbody implants) having standard sizes or shapes (stock implants).

SUMMARY

In one embodiment of the present disclosure, a method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In another embodiment of the present disclosure, a method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide a subtractive manufacturing operation.

In still another embodiment of the present disclosure, a method for designing a patient-specific implant includes obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In yet another embodiment of the present disclosure, a method for designing a patient-specific implant includes obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide a subtractive manufacturing operation.

In still another embodiment of the present disclosure, a method for designing a patient-specific implant includes obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine; determining whether the selected segments of the spine conform to the one or more correction guidelines, and generating three-dimensional implant geometry data configured to guide an automated manufacturing operation configured to produce an implant.

In yet another embodiment of the present disclosure, a computer system for designing a patient-specific implant includes at least one computer memory that is not a transitory signal, the at least one computer memory including instructions executable by at least one processor for obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In still another embodiment of the present disclosure, a computer system for designing a patient-specific implant includes at least one computer memory that is not a transitory signal, the at least one computer memory including instructions executable by at least one processor for obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In yet another embodiment of the present disclosure, a computer system for designing a patient-specific implant includes at least one computer memory that is not a transitory signal, the at least one computer memory including instructions executable by at least one processor for obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine, determining whether the selected segments of the spine conform to the one or more correction guidelines, and generating three-dimensional implant geometry data configured to guide an automated manufacturing operation configured to produce an implant.

In still another embodiment of the present disclosure, a patient-specific implant is manufactured by a process including obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In yet another embodiment of the present disclosure, a patient-specific implant is manufactured by a process including obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In still another embodiment of the present disclosure, a patient-specific implant is manufactured by a process including obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine, determining whether the selected segments of the spine conform to the one or more correction guidelines, and generating three-dimensional implant geometry data configured to guide an automated manufacturing operation configured to produce an implant.

BRIEF DESCRIPTION OF THE DRAWINGS

FIG. 25 is a side view of a patient with a neutral pelvis.

FIG. 26 is a side view of a patient with anterior pelvic tilt.

FIG. 27 is a side view of a patient with posterior pelvic tilt.

FIG. 28 is a side view of a pelvic tilt angle (PT) in a spine.

FIG. 29 is a side view of C7 sagittal vertebral axis (SVA) in a spine.

FIG. 30 is a side view of lumbar lordosis (LL) and pelvic incidence (PI) in a spine.

DETAILED DESCRIPTION

Figure 1:
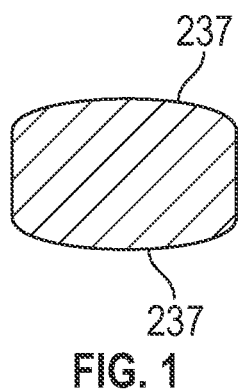
FIGS. 1-22 illustrate a variety of implants configured as intervertebral bodies and spacers, bone plates, pins, dowels, and the like, according to embodiments of the present disclosure.
Figure 2:
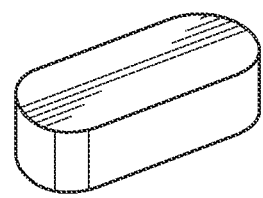
Figure 3:
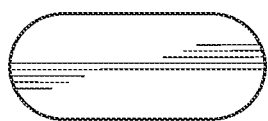
Figure 4:
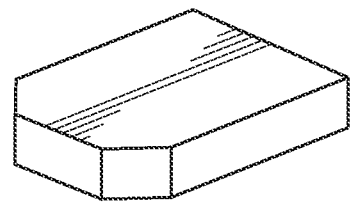
Figure 5:
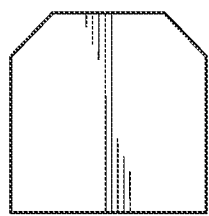
Figure 6:
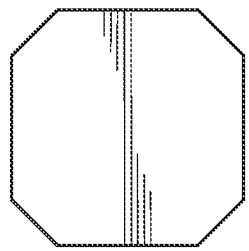

A patient-specific implant and an efficient method of producing the patient-specific implant are described in the embodiments herein. Patient-specific implants according to embodiments described herein may include interbody devices that have been custom-made to not only correspond with the particular anatomy of a patient, including shape and size, but also, to impart a particular type of correction to the patient. The term "interbody device," as used herein, refers generally to any interbody implant device (interbody device, interbody implant, interbody cage, fusion cage, or spine cage). The interbody devices are typically intended to be placed between two vertebral bodies. Oftentimes, the intervertebral disc is removed prior to the placement of the interbody device. The lower side of an interbody device is intended to abut at least a portion of an upper side (endplate) of a first vertebral body and the upper side of the interbody device is intended to abut at least a portion of a lower side (endplate) of a second vertebral body.

Insufficient contact and load transfer between the vertebral body and the interbody device can produce excessive load transfer in particular locations that can lead the cage to settle or subside into the vertebral body. Furthermore, insufficient contact area or pressure differentials between the interbody device and the vertebral bodies can produce micro-motions and/or macro-motions that can increase subsidence and result in expulsion of the interbody device from the disc space. It is believed by some that this insufficient contact area is due in part to the anatomical variability in the curvature of the vertebral endplates from vertebral level to vertebral level and from patient to patient. Additionally, low bone mineral density index or overaggressive decortications of the endplate can reduce the strength of the endplate and the ability to transfer load from one vertebral body to another. To reduce or eliminate these risks, surgeons carefully prepare the opposing vertebral endplates and attempt to insert an interbody device having as large a footprint (coverage area) as possible, in order to maximize the contact area of the interbody device on the vertebral endplates. When appropriate, the surgeon also places the interbody device on the apophyseal rings to provide as much support and load transfer as possible for spinal distraction, while also ensuring that the interbody device is securely nested within the disc space.

Pre-operative planning software may be utilized to determine or produce implants for surgery. There are two types of pre-operative planning software, those that are device specific and those that are device agnostic. Device specific pre-operative planning software typically provides a method to convert image data, such as CT (computed tomography) scan data, MRI (magnetic resonance induction) data, or x-ray data into two-dimensional or three-dimensional data. The converted data is then used to take measurements of the orthopedic problem (e.g., spine deformity), and to recommend one or more stock or standard model implants for treating the patient. One problem with this strategy is that treatment of the patient is limited to only the device models or sizes that are currently provided by medical device manufacturers. Oftentimes, none of the available models or sizes is appropriate for a particular patient and surgery plan. Complex or large corrections of the spine are typically not possible with the current state of the art in stock implants and device specific pre-operative planning software.

Device agnostic pre-operative planning software is typically used by a medical device manufacturer of a medical professional to provide a custom implant solution for a single patient. Software of this type often provides a method for converting image data (e.g., CT scan, etc.) to three-dimensional data that can be used to measure the orthopedic problem (e.g., spine deformity). Typically, a medical professional works in conjunction with a medical device manufacturer and the applicable regulatory body or controlling organization (FDA, IRB, etc.) to develop a custom device to treat the patient. While this process provides a personalized implant solution, it is an expensive and time-consuming process that is not feasible for most patients, medical professionals, or hospital payer systems.

The systems and methods described herein are configured to provide a three-dimensional shape that represents the ideal implant to fit into the negative space of the spine, once the spine receives the appropriate manipulation in the coronal, sagittal, and axial planes. In other words, the custom shape of the implant will at least partially provide and maintain the desired correction to the spine. Thus, the coronal, sagittal, and axial plane deformities of the spine are corrected, allowing restoration of the anatomical function of the spine. The correction may include both rotation and/or linear displacement along the degrees of freedom. For example, positive displacement along the x-axis, negative displacement along the x-axis, positive rotation around the x-axis, negative rotation around the x-axis, positive displacement along the y-axis, negative displacement along the y-axis, positive rotation around the y-axis, negative rotation around the y-axis, positive displacement along the z-axis, negative displacement along the z-axis, positive rotation around the z-axis, negative rotation around the z-axis. The systems and methods described herein utilize software that is configured to confirm conformity within the validated and regulatory cleared parameters. Upon software verification of the particular design of the interbody device, the software is then configured to capture patient specific data to complete the prescription and transmit the three-dimensional shape and prescription data to the medical device manufacturer. In some embodiments, the hospital or medical facility utilizing the software may itself be the medical device manufacturer. The systems and methods described herein further provide for the manufacture of the implant according to the specifics defined by the software-provided prescription, for example, by additive manufacturing techniques such as three-dimensional printing, or even by subtractive manufacturing techniques, such as CNC-manufacturing. Thus, the turn-around time and the expense, are similar to those for conventional stock implants, although the implants being provided are patient-specific. The patient has the combined benefit of a personalized implant treatment with a conventional price point and a short lead time. There is flexibility, combined with simplicity. The patient's ideal anatomical correction is coded into the prescription and the geometry of the ideal device is sent to a medical device manufacturer for fabrication, or may even be fabricated by a lab in the hospital or other medical treatment site, or remote site.

Figure 7:
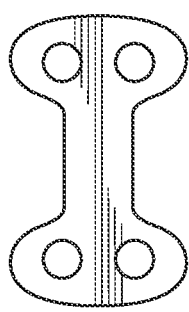
Figure 8:
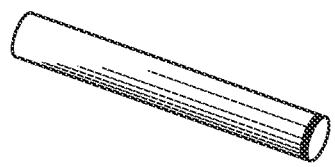
Figure 9:
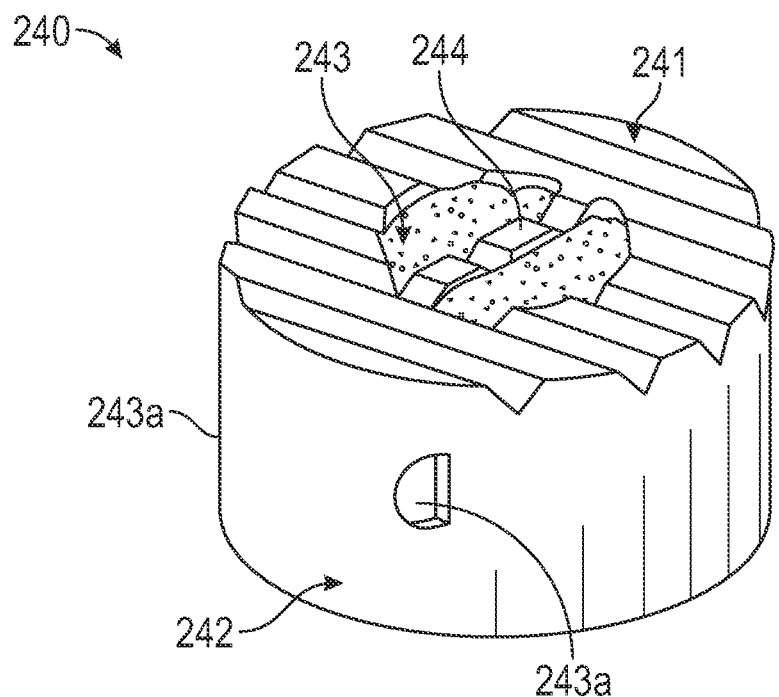
Figure 10:
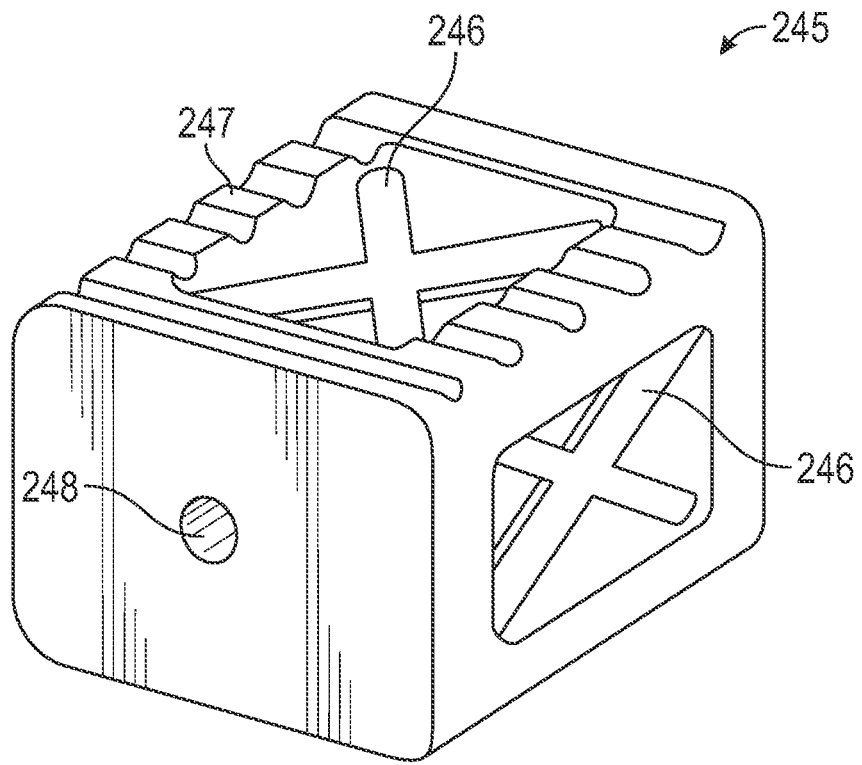
Figure 11:
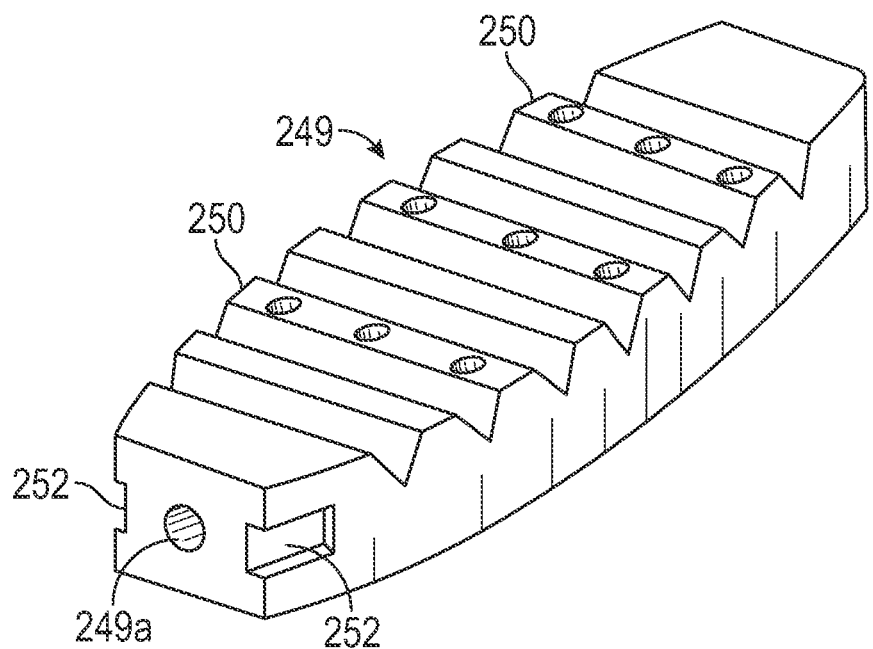

FIGS. 1-22 illustrate a variety of implants which may be produced by the systems and methods described herein, according to several embodiments of the present disclosure. FIG. 1 illustrates an intervertebral implant possessing biconvex surfaces 237 which are configured to match the curvatures of the vertebral endplates with which they come into contact. The biconvex surfaces 237 may each curve laterally (left to right), or curve anteriorly-posteriorly, or curve both laterally and anteriorly-posteriorly (e.g., a hemisphere or other three-dimensional convex shape). FIGS. 2-6 show various views of implants that are suitable for interbody use, including the oval footprints of FIGS. 2-3, the hexagonal footprints of FIGS. 4-5, or the octagonal footprint of FIG. 6. In some embodiments, other polygonal footprints may be utilized. In some embodiments, the footprint may comprise sides that are equal in length to each other, or in other embodiments, all of the sides may be equal in length to each other, or in other embodiments, none of the sides may be equal in length to each other. FIG. 7 shows a cervical bone plate for the fixation of adjacent cervical verterbrae. The bone plate spans two or more vertebrae, but does not necessarily fill the space between two vertebral endplates. The size and shape of the bone plate of FIG. 7, including the location of holes for screws, may be configured to maintain the cervical vertebrae in a particular relation to each other. FIG. 8 illustrates a cylindrical pin or dowel which may be keyed (not shown) to facilitate its installation. FIG. 9 illustrates an intervertebral implant 240 having a textured surface 241, e.g., roughenings, knurlings, ridges, and the like, to resist backing-out of the implant following its insertion in the intervertebral space. Surfaces 241 may converge to provide an anterior ramp configuration possessing a suitable lordotic angle or the surfaces may be essentially flat. The outer profile 242 of the implant can be round, oval, square, diamond-shaped, octagonal, hexagonal, etc., as requirements suggest. The implant can be provided with an opening 243 for receiving a quantity of osteogenic/osteoinductive material and/or a rigid reinforcing member 244 for added strength. The walls of the implant possess a pair of inserter instrument interfaces 243a (only one shown) for engagement with one end of an insertion tool. FIG. 10 depicts an open, or cage-like, structure 245 suitable for use as an anterior or posterior intervertebral implant. Cross braces 246 on one or more sides of the implant provide increased structural strength over that of a totally open configuration. The open space can be advantageously filled with an osteogenic/osteoinducting material. Texturized surfaces, e.g., ridges, 247 are provided to resist backing-out of the implant following its installation. Inserter interface 248 is intended to receive the distal (working end) of an implant insertion tool. FIG. 11 illustrates an intervertebral implant 249 possessing a position-retaining textured surface 250 (ridges) and a pattern of orifices communicating with the interior which possesses a void structure. The sides of the implant at one end thereof have a matching pair of implant inserter interfaces 252 which are intended to be grasped by an insertion tool. One end of the implant possesses an orifice 249a through which an osteogenic/osteoinductive material can be introduced into the interior void communicating channels of the implant.

Figure 12:
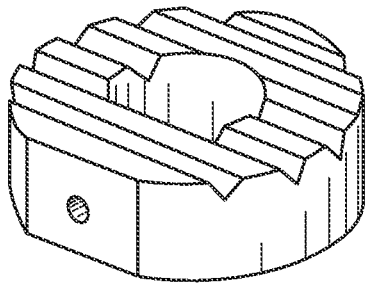
Figure 13:
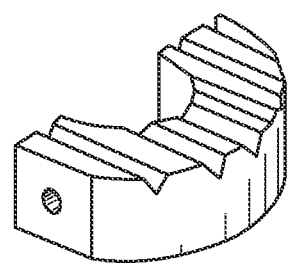
Figure 14:
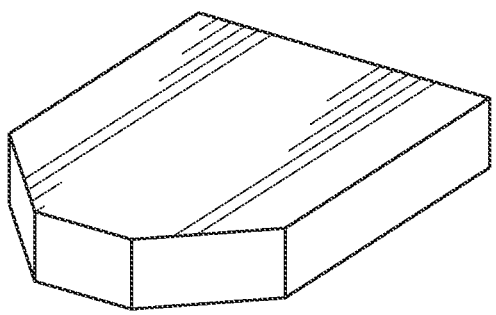
Figure 15:
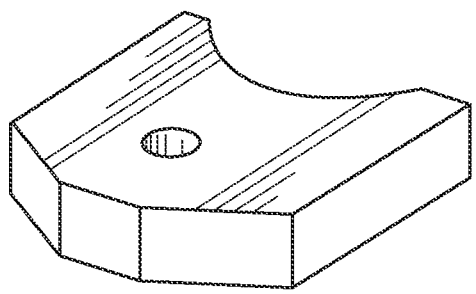
Figure 16:
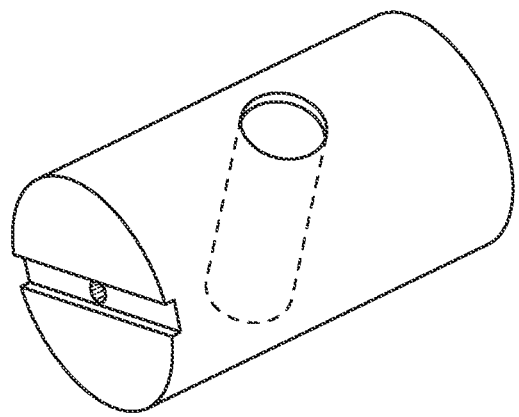
Figure 17:
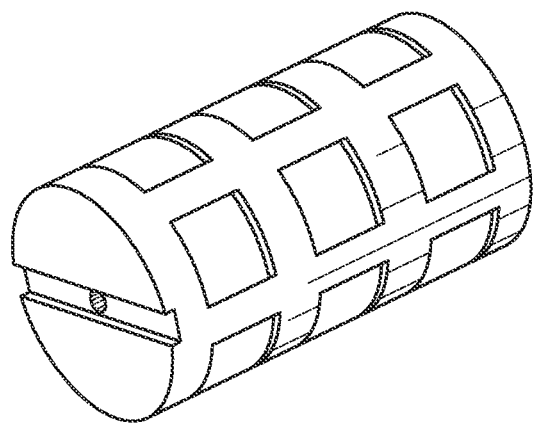
Figure 18:
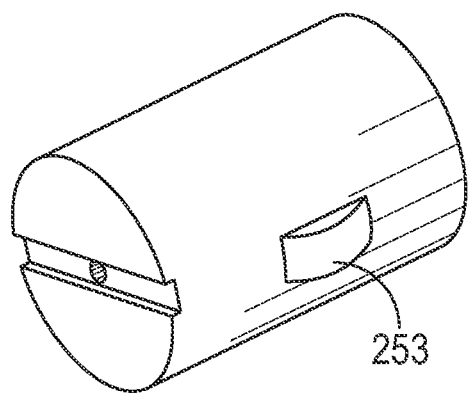
Figure 19:
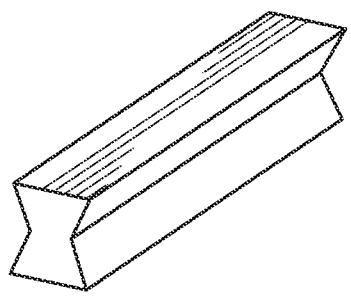
Figure 19:
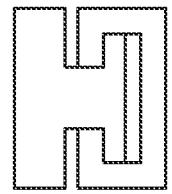
Figure 19:
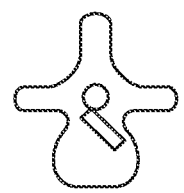
Figure 19:
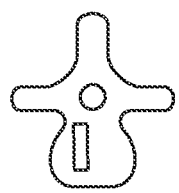
Figure 19:
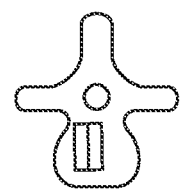
Figure 19:
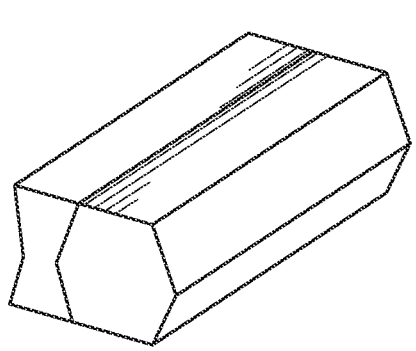
Figure 19:
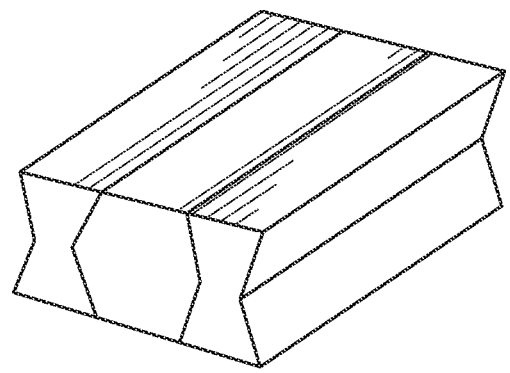
Figure 20:
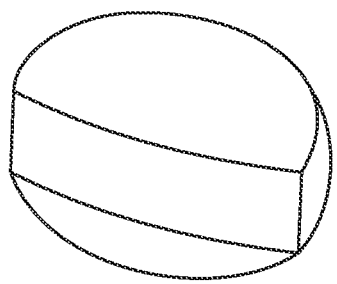
Figure 21:
Figure 22:
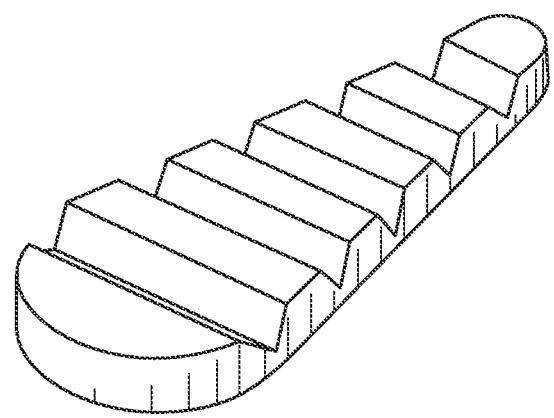

FIGS. 12-15 show various additional configurations of implants for insertion in the intervertebral space: FIG. 12 (an anterior ramp implant), FIG. 13 (a posterior ramp implant), FIG. 14 (a cervical spacer) and FIG. 15 (a cervical spacer including a radiused recess at one side). FIGS. 16-18 show various implants configured as intervertebral dowels. The implant of FIG. 16 is a solid structure with a through bore for receiving osteogenic/osteoinductive material. The implant of FIG. 17 possesses an open, or cage-like, structure which can be packed with osteogenic/osteoinductive material. The implant of FIG. 18 possesses at least one wing-like structure 253 on its longitudinal surface which prevents rotational displacement within the intervertebral space. Each of implants 16-18 possesses a slot and central hole for receiving the distal end of an insertion tool. FIG. 19 illustrates a transforaminal lumbar interbody fusion (TLIF) implant and its assembly from subunits. The implant of FIG. 19 may alternatively be used as a posterior lumbar interbody fusion (PLIF) implant. FIG. 20 depicts a convex anterior interbody ramp with openings communicating with the interior. FIG. 21 shows another embodiment of anterior interbody implant. FIG. 22 shows a solid anterior interbody implant presenting a large surface area for implant-vertebral endplate contact.

Figure 23:
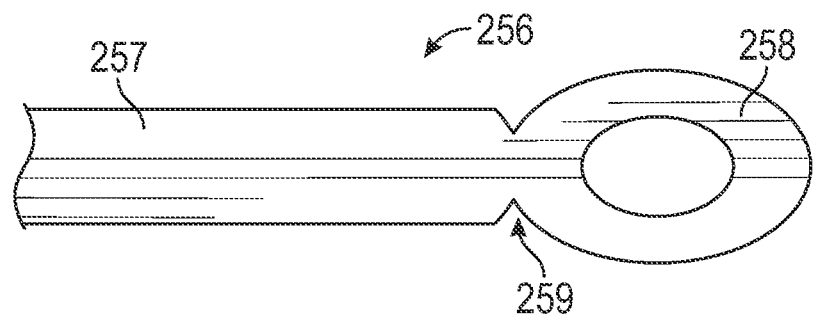
FIG. 23 illustrates the distal end of an integral implant insertion instrument and implant, according to an embodiment of the present disclosure.

FIG. 23 schematically illustrates in plan view the distal end 257 of an integral, or combined, implant insertion instrument and implant 256 wherein implant portion 258 specifically, an intervertebral implant, is joined to the distal end 257 of the instrument portion through a weakened, or break-away, site of attachment 259. Following insertion of the intervertebral implant in the intervertebral space, application of a sharp upward or downward movement of the implant insertion instrument will result in the distal end of the instrument cleanly breaking away, and separating from, the implant which remains in place. Alternatively, the site of attachment 259 may comprise any mechanism that allows the distal end 257 to releasably grip or maintain the implant 258, including, but not limited to: a clamp, an adhesive, epoxy, or hot melt attachment, a magnetic connection, a snap, a threaded attachment, a tapered attachment, a spring attachment, and a combination of any two or more of these attachment features. Custom instruments may even be produced by the systems and methods described herein. For example, a particular patient may have a deformity which requires an instrument having a particular angle that is not available in off-the-shelf instruments.

Figure 24:
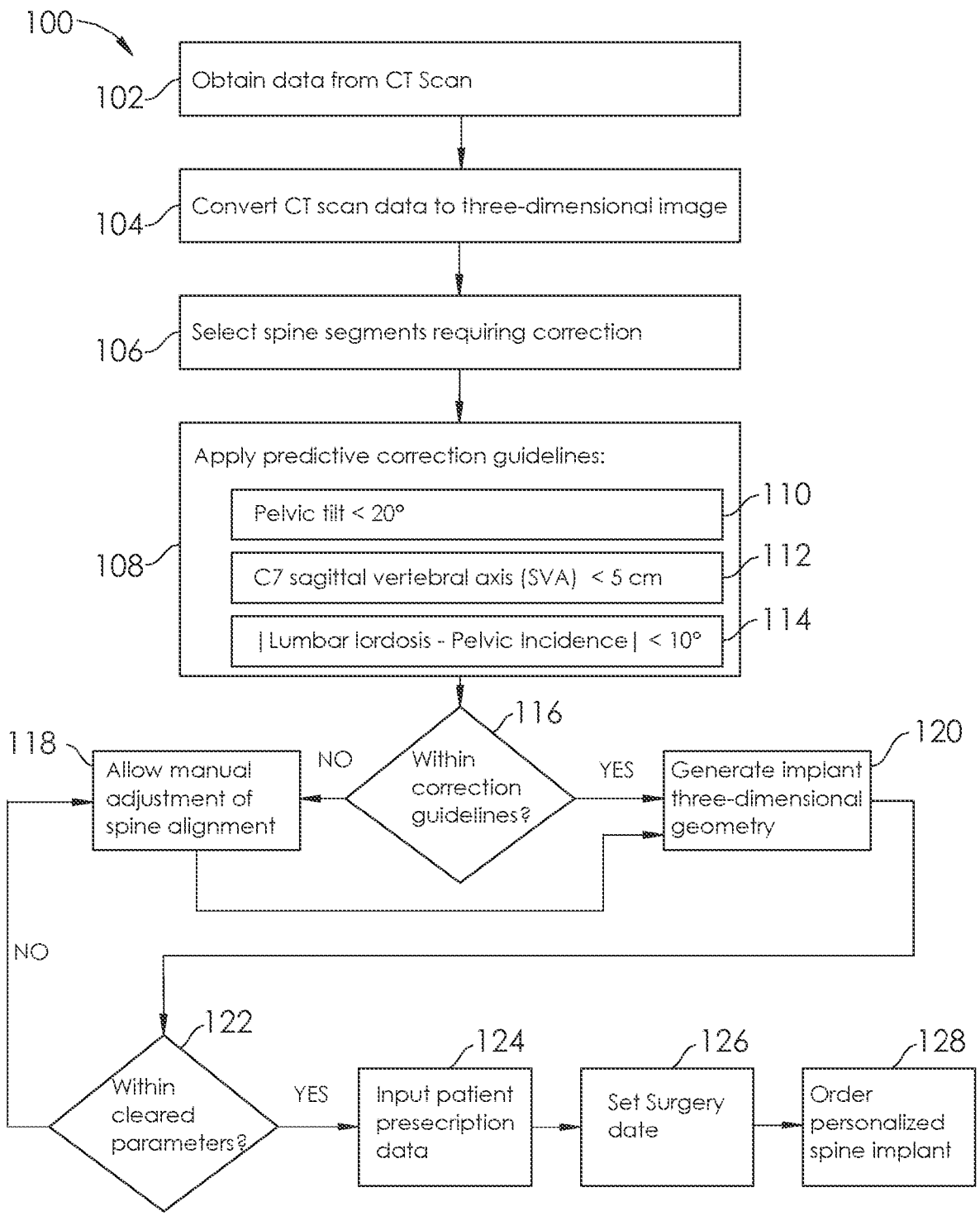
FIG. 24 is a flow chart of a method utilizing a system according to an embodiment of the present disclosure.

FIG. 24 illustrates a method 100 for utilizing a system for producing patient-specific implants. In step 102 scan data is obtained from a CT scan of a patient, for example, a CT scan that includes the spine of the patient, or at least the portion of interest in the spine. In other embodiments the scan data may comprise MRI scan data or x-ray data. In step 104, the CT scan data is converted into a three-dimensional image through software manipulation of the data. Typically, CT scan data is presented in a DICOM format, which includes individual slices of imaging data. A common slide thickness is one mm, though other thickness may be used, such as 0.25 mm, 0.5 mm, 1.5 mm, 2.0 mm, 2.5 mm, 3.0 mm and greater thicknesses. In step 106 spine segments may be selected for analysis. For example, a user interface that is associated with at least one computer memory that is not a transitory signal and which comprises instructions executable by at least one processor may be utilized to select a region of interest. In some cases, the region of interest may be a diseased or deformed portion of the spine, including a particular number of successive vertebrae and their surrounding soft tissue. In some cases, the entire spine may be selected. In some cases, only sacral and lumbar vertebrae and their surrounding soft tissue are selected. In some cases, only lumbar and thoracic vertebrae and their surrounding soft tissue are selected. In some cases, only cervical vertebrae and their surrounding soft tissue are selected.

Figure 32:
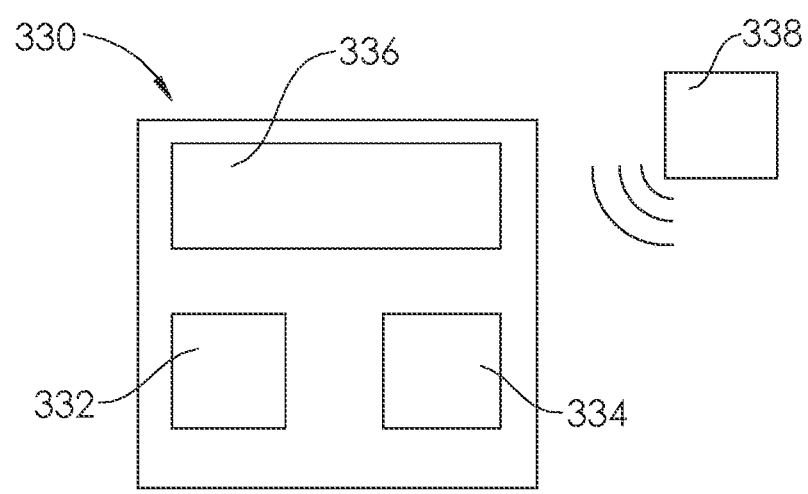
FIG. 32 is a plan view of a computer system, according to an embodiment of the present disclosure.

Turning to FIG. 32, a system 330 containing a memory 332 and a processor 334 may include any number of custom stand-alone devices, or any mobile device, such as an iPhone, smart phone, iPAD, smart watch, laptop or desktop computer. The system 330 may also include a user interface 336. The system 330 may also be configured to access the memory 332 remotely, for example, via internet browser access or other wireless means 338. The three-dimensional image can be converted into a form such that it can be manipulated by a user to measure anatomical deformities related to the disease (e.g., spine disease). The information can then be used by a medical professional, or technical or engineering professional in conjunction or collaboration with a medical professional, to design the optimized geometry of the corrected spine, thus allowing the design of an implant to treat the particular disease or malady.

In step 108, the computer memory is utilized to apply one or more predictive correction guidelines to the spine or to the selected portion of the spine, or at least a section thereof. A number of predictive correction guidelines may be utilized, but in one embodiment a set of three predictive guidelines is applied, relating to pelvic tilt 110, sagittal alignment 112, and lumbar lordosis 114. Legs 142 and torso 144 of a standing patient 140 are shown in FIG. 25. The patient 140 has a pelvis 146 that is in a neutral condition in relation to horizontal line 148. FIG. 26 illustrates a standing patient 141 who has an anterior pelvic tilt, with forwardly rotated pelvis 146 indicated by curved arrow and line 150 that is angled in relation to horizontal line 148. FIG. 27 illustrates a standing patient 143 who has a posterior pelvic tilt, with backwardly rotated pelvis 146 indicated by curved arrow and line 151 that is angled in relation to horizontal line 148. A spine 149 of a patient is shown in FIG. 28. A pelvic tilt angle PT is the angle created by the vertical axis 158 and a line 152 running from a midpoint of the sacral end plate 154 to the center 156 of the bifemoral heads. The predictive guideline regarding pelvic tilt 110 is defined by the equation wherein the pelvic tilt angle PT is less than 20 degrees (PT<20°). In some embodiments, the predictive guideline regarding pelvic tilt 110 may be defined by the equation 0°<PT<20°.

FIG. 29 illustrates a spine 149 having a positive C7 sagittal vertebral axis SVA. The C7 sagittal vertebral axis SVA is the distance from the plumb line 160 dropping from the center of the C7 vertebra to the posterior edge 162 of the upper sacral endplate surface 164. The predictive guideline regarding C7 sagittal vertebral axis (SVA) 112 is defined by the equation wherein the a C7 sagittal vertebral axis (SVA) less than 5 cm (SVA<5 cm). In some embodiments, the predictive guideline regarding the C7 sagittal vertebral axis (SVA) is defined by the equation wherein the absolute value of the C7 sagittal vertebral axis (SVA) is less than 5 cm (|SVA|<5 cm).

FIG. 30 illustrates a spine 149 with pelvic incidence PI and lumbar lordosis LL indicated. The pelvic incidence PI is the degree of sacral tilt with respect to the pelvis. More specifically, the pelvic incidence PI is the angle between the perpendicular line 168 to the center point 170 of the upper sacral endplate surface 164 and the line 172 between the center point 170 and center 156 of the bifemoral heads. Lumbar lordosis LL is the angle between L1 and S1. The predictive guideline regarding lumbar lordosis 114 is defined by the equation wherein an absolute value of the difference between pelvic incidence PI and lumbar lordosis LL is less than about 10 degrees. More specifically, the predictive guideline regarding lumbar lordosis 114 may be defined by the equation wherein an absolute value of the difference between pelvic incidence PI and lumbar lordosis LL is less than about 9 degrees. In some embodiments, other parameters may be used to formulate alternative or additional corrective guidelines. For example: C2-C7 angle, which evaluates the degree of cervical lordosis, and is the angle between the upper endplate surface of the C2 vertebra and the lower endplate surface of the C7 vertebra; thoracic kyphosis T1-T12 angle, which is the angle between the upper endplate surface of the T1 vertebra and the lower endplate surface of the T12 vertebra; thoracic kyphosis T4-T12 angle, which is the angle between the upper endplate surface of the T4 vertebra and the lower endplate surface of the T12 vertebra; C7 slope angle, which may predict cervical lordosis and thoracic kyphosis, and which is the angle between a horizontal line and the upper endplate surface of the C7 vertebra; sacral slope, which is the angle between a horizontal lune and the slope of the upper sacral endplate surface. Sacral slope SS may have a correlation between with pelvic incidence PI and pelvic tilt PT, such that SS≈PI−PT.

In decision point 116, the computer memory is utilized to determine whether, in the current state of the spine provided by the three-dimensional image, the predictive guidelines 110, 112, 114 are achieved. If one or more of the predictive guidelines 110, 112, 114 are not true for the spine segments selected, then a user may utilize a user interface to adjust spine alignment, as shown in step 118. For example, if the pelvic tilt is determined to be 20° or greater, a user may input or toggle an adjustment that changes the amount of correction in order to achieve a pelvic tilt less than 20°. If it is determined that the predictive guidelines are all achieved (whether user adjustment was or was not required), the system generates three-dimensional geometry in step 120. The three-dimensional geometry may in some cases define a single interbody device, or in other cases may define several interbody devices. In some cases, the three-dimensional geometry may define one or more interbody devices for a single level of the spine, or in other cases may define one or more interbody devices from two or more levels of the spine. In one embodiment, the DICOM data creates a point cloud map, which is then converted to multiple interconnected triangles to create a surface mesh. Based on known density discrepancies between bone and tissue, the three-dimensional mesh surface is parsed for bone surface data and converted to a three-dimensional image with volume. The converted data is saved into memory with a readable file format, such as .STL, .OBJ, or other CAD (computer-aided design) readable file format. In this CAD readable file format, the individual spine vertebral bodies can be isolated and manipulated in the axial, coronal, and sagittal planes.

After the three-dimensional geometry is generated, the system checks in decision point 122 whether the particular correction is within cleared parameters. For example, within a particular amount of correction that is approved under a regulatory clearance; or, within a particular amount of correction that is approved under an IRB-controlled or FDA-controlled clinical trial. In addition to, or instead of, the amount of correction, other parameters may determine whether the three-dimensional geometry performs within cleared parameters in decision point 122. For example, the total volume or total mass of the implant(s) may be controlled, such that it must be within a particular range, or that it must be below a certain amount per unit weight of patient. If the correction (or other parameters) is not within the cleared range(s), user-initiated input may be performed, as in step 118. In some embodiments, the system may suggest the amount to adjust each parameter of spine alignment, allowing the user to accept this suggestion, or to choose a different value of change. In some cases, step 122 may not be necessary, for example, when certain procedures do not have implant-based regulatory limitations. A particular manner of validating a cleared amount of correction, is to check the three-dimensional envelope of the spine implant at both the maximum material condition and the least material condition. For example, an FDA clearance may take into account both of these conditions, in one or more patient indications.

Once the three-dimensional geometry is accepted by the user, and, if applicable, by the limitations of step 122, a patient prescription can be created in step 124. The patient prescription may comprise one or more three-dimensional files that are used in additive manufacturing, including, but not limited to: .AMF, .X3D, Collada (Collaborative Design Activity), .STL, .STP, .STEP, or .OBJ. The patient prescription may alternatively comprise one or more three dimensional files, including, but not limited to: .IGS, .STP, .STEP, .3ds, .blend, .dae, .ipt, .skp, .fbx, .off, .ply, .sldprt, .sldasm, and .X_T. In some cases, the patient prescription may also include one or more two-dimensional files, for example, to map or guide the surgical treatment, or to stage the utilization of each implant. The two-dimensional files may include, but are not limited to: .dwg, .dwf, .dxf, .pdf, or .acis. The surgery can be scheduled in step 126, and the personalized implant can be ordered in step 128.

The step 128 may include using the three-dimensional files to manufacture the implant using one or more additive manufacturing or subtractive manufacturing methods. Additive manufacturing methods include, but are not limited to: three-dimensional printing, stereolithography (SLA), selective laser melting (SLM), powder bed printing (PP), selective laser sintering (SLS), selective heat sintering (SHM), fused deposition modeling (FDM), direct metal laser sintering (DMLS), laminated object manufacturing (LOM), thermoplastic printing, direct material deposition (DMD), digital light processing (DLP), inkjet photo resin machining, and electron beam melting (EBM). Subtractive manufacturing methods include, but are not limited to: CNC machining, EDM (electrical discharge machining), grinding, laser cutting, water jet machining, and manual machining (milling, lathe/turning).

Following the manufacture of the implant, a bone-friendly scaffold is created for fusion to one or more vertebrae. The implant may comprise one or more of the following materials: titanium, titanium alloy, titanium-6AL-4V, tantalum, and PEEK (polyether ether ketone). The implant may also comprise/be coated with a biologic material. Examples of potential biological materials include, but are not limited to: hydroxylapetite (hydroxyapetite), recombinant human bone morphogenic proteins (rhBMP-2, rhBMP-7), bioactive glass, beta tri-calcium phosphate, human allograft (cortical and/or cancellous bone), xenograft, other allograft, platelet rich plasma (PRP), stem cells, and other biomaterials. In addition, synthetic ceramics having osteogenic properties may be utilized. The manufacture of the implant may be further guided by patient information, including patient age, patient weight, or prior patient surgical history. For example, a patient with a high BMI (body mass index) can require a stiffer or stronger implant, such as an implant made with a different material (e.g., having mechanical characteristics) and/or an implant having thicker material cross-sectional dimensions. The lattice structure forming the implant can be optimized to meet the patient's biomechanical needs for stability. Additionally, a patient with a low BMI and/or with osteoporotic bone or osteopenia can benefit from an implant having lower stiffness (higher flexibility), thus helping to reduce the risk of subsidence. Furthermore, a patient having a previously failed fusion may be at risk for adjacent level disc disease and/or proximal joint kyphosis. An implant can be tailored to alleviate this particular situation.

Figure 31:
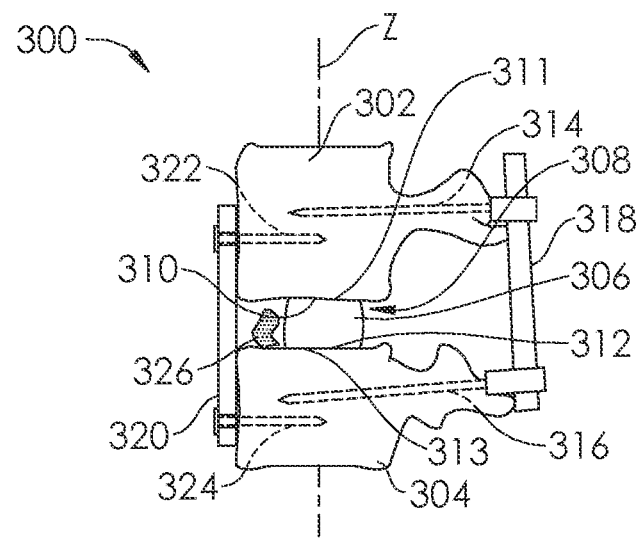
FIG. 31 is a side view of an interbody device implanted between two vertebrae of a patient.

FIG. 31 illustrates a portion of a spine 300 including a first vertebra 302 and a second vertebra 304. In use, a patient-specific interbody device 306 manufactured using according to the embodiments described herein is placed by a user into the negative space 308 of the spine 300, and engaged between a lower endplate surface 310 of the first vertebra 302 and an upper endplate surface 312 of the second vertebra 304. An upper surface 311 of the interbody device 306 engages the lower endplate surface 310 of the first vertebra 302 and a lower surface 313 of the interbody device 306 engages the upper endplate surface 312 of the second vertebra 304. The interbody device 306 is configured to maintain the distance between the first vertebra 302 and the second vertebra 304, and more specifically, between the lower endplate surface 310 of the first vertebra 302 and the upper endplate surface 312 of the second vertebra 304 (e.g., along the Z-axis). The interbody device 306 may also be configured to maintain X-axis and/or Y-axis position (not shown) between the first vertebra 302 and the second vertebra 304, and may be configured to maintain rotational orientation of one of both of the first vertebra 302 and the second vertebra 304, for example, in relation to the X-axis, Y-axis, and/or Z-axis. In some embodiments, pedicle screws 314, 316 and a rod 318 may be used to further lock the orientation in place. In other embodiments, a plate 320 and screws 322, 324 may be used to further lock the orientation in place. Though both the rod 318 and plate 320 are shown coupled to the first vertebra 302 and the second vertebra 304 in FIG. 31, commonly only one of two would be used, though it is possible to incorporate both in certain situations. Bone graft 326 or other biological materials may be used to further promote fusion of the first vertebra 302 and the second vertebra 304, and may be implanted within the negative space 308.

The systems and methods described herein may be utilized to correct other physiological ailments requiring a patient-specific implant. For example, wedge-shaped implants for maintaining wedge osteotomies in the spine, or other orthopedic areas such as the hip, jaw, chin or knee for arthritic or non-arthritic conditions, may be designed with the teachings of the present disclosure. Particular procedures include: high tibial osteotomy (tibia), distal femoral osteotomy (femur), Evans wedge or Cotton wedge (foot and ankle).

The ranges disclosed herein also encompass any and all overlap, sub-ranges, and combinations thereof. Language such as "up to," "at least," "greater than," "less than," "between," and the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

I claim:

1. A computer-implemented method for designing a patient-specific implant, comprising:
   receiving one or more surgical adjustments to patient spinal anatomy;
   generating an updated virtual model of the patient spinal anatomy based on the surgical adjustments;
   measuring one or more geometric characteristics of the patient spinal anatomy from the updated virtual model;
   comparing a measured value of at least one of the one or more geometric characteristics to one or more criteria associated with the at least one geometric characteristic,
   in response to the measured value conforming with the one or more criteria based on the comparison, generating implant geometry data based at least in part on the updated virtual model and/or the measured value, wherein the implant geometry data includes a three-dimensional geometry of a patient-specific implant; and
   in response to the measured value not conforming with the one or more criteria based on the comparison, requiring additional adjustment to the patient spinal anatomy such that the geometric characteristic conforms with the one or more criteria before generating the implant geometry data; and
   manufacturing the patient specific implant based on the implant geometry data.

2. The method of claim 1 wherein the one or more geometric characteristics include pelvic tilt, sagittal alignment, and/or lumbar lordosis.

3. The method of claim 2 wherein the one or more criteria includes a predetermined range of values and/or a predetermined threshold for one or more of:
   pelvic tilt,
   sagittal alignment, and/or
   lumbar lordosis.

4. The method of claim 1 wherein the one or more geometric characteristics include sagittal vertical axis, lumbar vertical axis, coronal offset, cobb angle, and/or coronal angle.

5. The method of claim 1 wherein the virtual model is a three-dimensional model of the patient spinal anatomy, the method further comprising generating the three-dimensional model of the patient spinal anatomy based on image data before receiving the one or more surgical adjustments.

6. The method of claim 5 wherein the three-dimensional model can be manipulated by a user for receiving the one or more surgical adjustments.

7. The method of claim 1 wherein the implant geometry data includes manufacturing instructions configured to guide a manufacturing system to manufacture the patient-specific implant.

8. The method of claim 1 wherein the patient-specific implant is designed to provide the one or more surgical adjustments when implanted in the patient.

9. The method of claim 8 wherein the patient-specific implant includes at least two interbody devices.

10. A system for designing a patient-specific implant, comprising:
at least one processor;
at least one non-transitory computer memory comprising instructions executable by the at least one processor for:
receiving one or more surgical adjustments to patient spinal anatomy;
generating an updated virtual model of the patient spinal anatomy based on the surgical adjustments;
measuring one or more geometric characteristics of the patient spinal anatomy from the updated virtual model;
comparing a measured value of at least one of the one or more geometric characteristics to one or more criteria associated with the at least one geometric characteristic,
in response to the measured value conforming with the one or more criteria based on the comparison, generating implant geometry data based at least in part on the updated virtual model and/or the measured value, wherein the implant geometry data includes a three-dimensional geometry of a patient-specific implant; and
in response to the measured value not conforming with the one or more criteria based on the comparison, requiring additional adjustment to the patient spinal anatomy such that the geometric characteristic conforms with the one or more criteria before generating the implant geometry data; and
a manufacturing system configured to manufacture the patient-specific implant using the implant geometry data.

11. The system of claim 10 wherein the one or more geometric characteristics include pelvic tilt, sagittal alignment, sagittal vertical axis, coronal angle, cobb angle, and/or lumbar lordosis.

12. The system of claim 11 wherein the one or more criteria includes a predetermined range of values and/or a predetermined threshold for one or more of:
pelvic tilt,
sagittal vertical axis,
sagittal alignment, and/or
lumbar lordosis.

13. A computer-implemented method for designing a patient-specific implant, comprising:
generating a first virtual model depicting patient spinal anatomy;
receiving one or more surgical adjustments to the patient spinal anatomy;
generating a second virtual model depicting the patient spinal anatomy with the one or more surgical adjustments;
measuring one or more geometric characteristics of the patient spinal anatomy from the second virtual model;
determining whether a measurement obtained for at least one of the one or more geometric characteristics of the patient spinal anatomy conforms to one or more criteria associated with the at least one geometric characteristic; and
generating three-dimensional implant geometry data based at least in part on the second virtual model and in response to the measurement of the at least one of the one or more geometric characteristics conforming with the one or more criteria; and
causing a manufacturing system to use the implant geometry data to manufacture a patient-specific implant configured to provide the one more surgical adjustments when implanted in the patient.

14. The method of claim 13 wherein the one or more geometric characteristics include pelvic tilt, sagittal alignment, and/or lumbar lordosis.

15. The method of claim 14 wherein the one or more criteria includes a predetermined range of values and/or a predetermined threshold for one or more of:
pelvic tilt,
sagittal alignment, and/or
lumbar lordosis.

16. The method of claim 13 wherein the one or more geometric characteristics include sagittal vertical axis, lumbar vertical axis, coronal offset, cobb angle, and/or coronal angle.

17. The method of claim 13, further comprising receiving image data of native patient spinal anatomy, and wherein generating the first virtual model includes generating the first virtual model based on the received image data.

18. The method of claim 13 wherein generating the second virtual model includes updating the first virtual model to reflect the one or more surgical adjustments.

19. The method of claim 13 wherein the patient-specific implant includes at least two interbody devices.

20. A system for designing a patient-specific implant, comprising:
at least one processor;
at least one non-transitory computer memory comprising instructions executable by the at least one processor for:
generating a first virtual model depicting patient spinal anatomy;
receiving one or more surgical adjustments to the patient spinal anatomy;
generating a first virtual model depicting patient spinal anatomy;
receiving one or more surgical adjustments to the patient spinal anatomy;
generating a second virtual model depicting the patient spinal anatomy with the one or more surgical adjustments;
measuring one or more geometric characteristics of the patient spinal anatomy from the second virtual model;
determining whether a measurement obtained for at least one of the one or more geometric characteristics of the patient spinal anatomy conforms to one or more criteria associated with the at least one geometric characteristic; and generating three-dimensional implant geometry data based at least in part on the second virtual model and in response to the measurement of the at least one of the one or more geometric characteristics conforming with the one or more criteria; and a manufacturing system configured to use the implant geometry data to manufacture a patient-specific implant designed to provide the one or more surgical adjustments when implanted in the patient.

21. A computer-implemented method for designing a patient-specific implant, the method comprising:

generating a virtual model of patient spinal anatomy that includes a proposed surgical correction to the patient spinal anatomy;

measuring one or more geometric characteristics of the patient spinal anatomy with the proposed surgical correction from the virtual model;

comparing a measured value of at least one of the one or more geometric characteristics to one or more criteria associated with the at least one geometric characteristic;

in response to the measured value conforming with the one or more criteria based on the comparison, generating implant geometry data based at least in part on the updated virtual model and/or the measured value, wherein the implant geometry data includes a three-dimensional geometry of a patient-specific implant;

in response to the measured value not conforming with the one or more criteria based on the comparison, requesting additional adjustment to the proposed surgical adjustment to patient spinal anatomy such that the geometric characteristic conforms with the one or more criteria before generating the implant geometry data; and manufacturing the patient specific implant based on the implant geometry data.

22. The computer-implemented method of claim 21 wherein the one or more geometric characteristics include pelvic tilt, sagittal alignment, lumbar lordosis, sagittal vertical axis, lumbar vertical axis, coronal offset, cobb angle, and/or coronal angle.

23. The computer-implemented method of claim 22 wherein the one or more criteria includes a predetermined range of values and/or a predetermined threshold for one or more of pelvic tilt, sagittal alignment, lumbar lordosis, sagittal vertical axis, lumbar vertical axis, coronal offset, cobb angle, and/or coronal angle.

24. A system for designing a patient-specific implant, comprising:

at least one processor;

at least one non-transitory computer memory comprising instructions executable by the at least one processor for:

generating a virtual model of patient spinal anatomy that includes a proposed surgical correction to the patient spinal anatomy, measuring one or more geometric characteristics of the patient spinal anatomy with the proposed surgical correction from the virtual model, comparing a measured value of at least one of the one or more geometric characteristics to one or more criteria associated with the at least one geometric characteristic, in response to the measured value conforming with the one or more criteria based on the comparison, generating implant geometry data based at least in part on the updated virtual model and/or the measured value, wherein the implant geometry data includes a three-dimensional geometry of a patient-specific implant, and in response to the measured value not conforming with the one or more criteria based on the comparison, requesting additional adjustment to the proposed surgical adjustment to patient spinal anatomy such that the geometric characteristic conforms with the one or more criteria before generating the implant geometry data; and a manufacturing system configured to manufacture the patient-specific implant using the implant geometry data.

* * * * *